United States Patent [19]

Nakano et al.

[11] Patent Number: 4,687,675
[45] Date of Patent: Aug. 18, 1987

[54] METHOD FOR THE PRODUCTION OF ENDOSSEOUS IMPLANTS

[75] Inventors: Kazuhiko Nakano, Katano; Keiichirou Watanabe, Toyonaka, both of Japan

[73] Assignee: Sumitomo Chemical Company, Osaka, Japan

[21] Appl. No.: 865,089

[22] Filed: May 20, 1986

[30] Foreign Application Priority Data

May 20, 1985 [JP] Japan ................................. 60-108030

[51] Int. Cl.$^4$ ............................................. B05D 1/10
[52] U.S. Cl. .......................................... 427/2; 427/34; 427/352; 427/422; 427/423; 128/92 YQ; 128/92 YG; 623/22; 623/23
[58] Field of Search ..................... 427/34, 422, 423, 2, 427/336, 352; 128/92 YO, 92 YOG; 623/22, 23

[56] References Cited

U.S. PATENT DOCUMENTS 4,146,936  4/1979  Aoyagi et al. ..................... 427/423
4,223,412  9/1980  Aoyagi et al. ........................ 623/16

*Primary Examiner*—Shrive P. Beck
*Attorney, Agent, or Firm*—Birch, Stewart, Kolasch and Birch

[57] ABSTRACT

An improved method for the production of endosseous implants is disclosed. The method includes thermally spraying a hydroxyapatite-containing powder onto the surface of a metallic core material, and treating the resultant product with an aqueous solution which does not substantially dissolve the hydroxyapatite but can dissolve calcium oxide, to thereby dissolve out alkaline components. The endosseous implants of this invention have excellent mechanical properties and excellent affinity to the living body without hematolysis, and hence, are useful for the treatment or recovery of defective or lost bones, joints and tooth roots.

8 Claims, No Drawings

METHOD FOR THE PRODUCTION OF ENDOSSEOUS IMPLANTS

This invention relates to an improved method for the production of endosseous implants, and more particularly, to a method for the production of endosseous implants comprising thermally spraying a hydroxyapatite-containing powder onto a metallic core material with a thermal spray apparatus and then treating the resultant endosseous implant material with a specific aqueous solution for dissolving out alkaline components therefrom.

TECHNICAL BACKGROUND AND PRIOR ART

Implant materials are used for the recovery of lost parts of living bodies or their functions by inserting them into living bodies or by replacing the lost parts with the materials. Endosseous implants include artificial bones, artificial joints, artificial tooth roots, and the like.

The Endosseous implants have recently been developed, and as the materials for the implants, attention has been given to metallic materials such as cobalt-chromium alloys, titanium, tantalum, etc.; ceramics such as oarbon-aluminum oxide-calcium phosphate; and single crystals such as sapphire. Implants made from these materials have widely been used for the treatment and recovery of defective or lost parts of bones and tooth roots with succesful results. However, these materials are not necessarily satisfactory as a material for a living body in terms of affinity to a living body, safety, corrosion resistance, strength, toughness, durability, etc. That is, although the metallic materials are superior in mechanical characteristics such as strength and toughness, they have some problems in their affinity to a living body. instance, metal ions are dissolved out therefrom in living body and affect a toxic action to bone cells and further they give an undesirable effect on the bone-formation due to high thermal conductivity. Among the metallic materials, tantalum is excellent in the corrosion resistance, but it has less processability.

On the other hand, ceramic materials and single crystalline materials have excellent affinity to the living body, but have inferior toughness and hence have less impact strength. Particularly, hydroxyapatite is composed of calcium phosphate, i.e. the same material as the components of bones and hence has excellent affinity to the living body, but the sintered product thereof shows less strength.

From these viewpoints, attention has recently been paid to an implant material which is produced by thermally spraying ceramic materials such as hydroxyapatite having excellent affinity to the living body onto the surface of a metallic core material having high mechanical characteristics by a thermal spray method such as a thermal plasma spray. This material has excellent affinity to the living body, excellent mechanical strength and impact resistance, and hence is expected to be the best one as an implant material. According to the present inventors' study, however, since it is produced by thermally spraying a powder containing hydroxyapatite onto the surface of the metallic core material with a plasma flame at a high temperature, the powder of hydroxyapatite which is easily decomposed by heat is exposed to such a high temperature (while only for a very short period of time), and thereby the hydroxyapatite is partially decomposed. The present inventors have found that when such a material is dipped in a physiological saline solution, the decomposed components, particularly alkaline components, are dissolved out to make alkaline the solution. This suggests that when such an implant material is used, it may induce undesirable side effects such as hematolysis.

SUMMARY OF THE INVENTION

Under these circumstances, the present inventors have studied the prevention of dissolving out such alkaline components from the implant material produced by thermally spraying a hydroxyapatite-containing powder onto the surface of a metallic core material by a thermal plasma spray or the like and have now found that when the product obtained by the thermal spray is treated with an aqueous solution which does not substantially dissolve hydroxyapatite but can dissolve calcium oxide, the alkaline dissolving components are removed and the thus-treated product does not exhibit any hematolytic action in a hematolysis test.

Accordingly, an object of The present invention is to provide an improved method for the production of endosseous implants having no hematolysis. Another object of the invention is to provide a method for the after-treatment of the implant material obtained by thermally spraying a hydroxyapatite-containing powder onto the surface of a metallic core material in order to remove the alkaline dissolving components therefrom. These and other objects and advantages of the invention will be apparent to those persons skilled in the art from the following description.

DETAILED DESCRIPTION OF THE INVENTION

The method of the present invention comprises thermally spraying a hydroxyapatite-containing powder onto the surface of a metallic core material by a thermal spray apparatus, such as a thermal plasma spray apparatus and then treating the resultant product with an aqueous solution which does not substantially dissolve hydroxyapatite, but can dissolve calcium oxide.

The hydroxyapatite-containing powder includes powdery hydroxyapatite, a powdery mixture of powdery hydroxyapatite with a powder of a stable oxide such as alumina, zirconia, etc. These powders preferably have a particle size of 10 $\mu$m to 300 $\mu$m and good flow properties. For instance, a conventional synthetic hydroxyapatite obtained by precipitating from an aqueous solution and sintering at 700° to 1,200° C. is usually composed of coagulated particles having a particle size ranging over several microns, and they have inferior flow properties and hence are not suitable for thermal spraying. Accordingly, these conventional hydroxyapatite powders are preferably granulated into granules having a particle size of several microns or more by a suitable granulating method such a spray granulting method. More preferably, the hydroxyapatite particles have a primary particle size as large as possible. In the case of a mixture of hydroxyapatite with oxide particles such as alumina or zirconia particles, it is preferable to use particles which are made and sold for the purpose of thermal spraying, or particles which are produced by an electric melting method and have a large paricle size and good flow properties.

The metallic materials used for the core material include various metallic materials such as titanium, a titanium alloy, a cobalt-chromium alloy, and the like. It is preferable to make the surface thereof rough by treating the material with sand-blast etc. so that the thermally sprayed material can easily be adhered onto the surface thereof.

The thermal spray can be performed by any conventional a thermal spray methods, such as thermal plasma spray method, a thermal flame spray method, or the like.

After the thermal spray, the sprayed product is subjected to the after-treatment with an aqueous solution which does not substantially dissolve the hydroxyapatite but can dissolve calcium oxide in order to remove the alkaline dissolving components. The aqueous solution includes an aqueous solution of ingredients such as an inorganic salt selected from ammonium chloride, magnesium chloride, ammonium nitrate and magnesium nitrate, a succharide selected from sucrose, fructose, glucose and arabinose, ethylene glycol, glycerol, etc. These ingredients may be used alone or in a combination thereof. It is not suitable to use an aqueous solution of mineral acids such as hydrochloric acid, nitric acid, etc., which also dissolve hydroxyapatite. The concentration of the aqueous solution is not specified but is preferably as high as possible because of a larger dissolving force. However, if the concentration is too high, the aqueous solution may occasionally result in an increase of viscosity to an unsuitable degree depending on the properties of the ingredients. Hence the most suitable concentration may be determined in each kind of ingredient, but the concentration of inorganic salt is usually in the range of 1 to 20% by weight, preferably 5 to 15% by weight, that of succharide is usually in the range of 5 to 50% by weight, preferably 5 to 40% by weight, and that of ethylene glycol or glycerol is usually in the range of 5 to 90% by weight, preferably 10 to 80% by weight. The after-treatment may be carried out at any temperature unless it is higher than the boiling point of the aqueous solution, but is usually carried out at room temperature or at an elevated temperature, preferably at 10° to 100° C., more preferably at 20° to 80° C. The after-treatment may usually be carried out by dipping the thermally sprayed product into the aqueous solution, but may be done by washing (showering) the product with the aqueous solution.

After the after-treatment, the thermally sprayed product thus treated is washed well with hot water, etc. in order to wash off the ingredients in the aqueous solution and is then dried.

The thermally sprayed product thus obtained has no alkaline dissolving components and hence does not show any hematolysis in the hematolysis test.

Thus, according to this invention, there is solved the problem of hematolysis which is observed in the known endosseous implants produced by the thermal spraying of a hydroxy-appatite-containing powder onto a metallic core material, while maintaining the excellent mechanical strength, impact resistance and affinity to the living body. Hence the product of the present invention is particularly useful as an endosseous implant for the treatment and recovery of defective or lost bones, joints and tooth roots.

This invention is illustrated by the following examples but should not be construed to be limited thereto.

EXAMPLE 1

To multiple strips of metallic titanium plate (50×5×0.5 mm), the surfaces of which are roughened brushing with a sandblast, is thermally sprayed a hydroxyapatite powder (granulated by spray granulation, medium particle size: 50 μm) in a usual manner with a thermal plasma spray apparatus to a thickness of the thermally sprayed layer of 150 μm (this product is referred to as "Sample No. 1").

The above product is dipped in a 10% aqueous ammonium chloride solution at 75° C. for 24 hours, and washed with hot water until chlor ion is no longer detected, and then dried (this product is referred to as "Sample No. 2").

These samples were subjected to the following tests.

A test solution is prepared by mixing ethanol (5 ml) and a commercially available physiological saline solution (95 ml). 100 strips of Sample No. 2 were dipped in the test solution, and they were heated under sealing at 70° C. for 24 hours and thereafter allowed to stand until the temperature became room temperature. The pH value of this test solution was measured. As a result, it had a pH 6.8 (neutral).

Rabbit blood (defibrilated) (0.1 ml) was added to the test solution as treated above (10 ml), and the mixture was allowed to stand at 37° C. for 24 hours. As a result, no hematolysis was observed.

On the other hand, the above tests were repeated by using Sample No. 1. As a result, the test solution had pH 11.5 (alkaline) and showed clear hematolysis.

EXAMPLE 2

To multiple strips of the same metallic titanium plate as used in Example 1 was thermally sprayed a powdery mixture of the granulated hydroxyapatite (as used in Example 1) (80 parts by weight) and an alumina powder prepared by an electric melting method (20 parts by weight) by a thermal plasma spray apparatus to a thickness of the thermally sprayed layer of 200 μm (this product is referred to as "Sample 3").

The above product is dipped in a 10% aqueous ammonium chloride solution at 75° C. for 24 hours, and washed with hot water until chlor ion is no longer detected and dried (the product is referred to as "Sample 4").

These products, Sample Nos. 3 and 4, were tested in the same manner as described in Example 1. As a result, the solution of No. 3 had pH 10.8, and that of No. 4 had pH 6.6. Sample No. 3 showed hematolysis but Sample No. 4 did not show hematolysis.

EXAMPLE 3

Sample No. 3 as prepared in Example 2 is dipped in an 8% aqueous sucrose solution at room temperature for 24 hours, washed well with hot water and then dried (this product is referred to as "Sample No. 5).

The above product was subjected to the same tests as described in Example 1. As a result, it had pH 7.0 and showed no hematolysis. The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for the production of endosseous implants comprising thermally spraying a hydroxyapatite-containing powder to the surface of a metallic core material, and treating the thermally sprayed product with an aqueous solution which does not substantially dissolve the hydroxyapatite but can dissolve calcium oxide to thereby dissolve out the alkaline components from the product.

2. The method according to claim 1, wherein the aqueous solution is an aqueous solution of an inorganic salt selected from the group consisting of ammonium chloride, magnesium chloride, ammonium nitrate and magnesium nitrate.

3. The method according to claim 1, wherein the aqueous solution is an aqueous solution of a succharide selected from the group consisting of sucrose, glucose, fructose and arabinose.

4. The method according to claim 1, wherein the aqueous solution is an aqueous solution of ethylene glycol and/or glycerol.

5. The method according to claim 2, wherein the inorganic salt is ammonium chloride.

6. The method according to claim 3, wherein the succharide is sucrose.

7. The method according to claim 1, wherein the aqueous solution is an aqueous solution of ammonium chloride and sucrose.

8. The method according to claim 1, wherein the thermal spraying is plasma spraying.

* * * * *